US00PP36156P2

(12) United States Plant Patent
Heuger

(10) Patent No.: US PP36,156 P2
(45) Date of Patent: Sep. 24, 2024

(54) ***HELLEBORUS* PLANT NAMED 'HM 1214'**

(50) Latin Name: ***Helleborus ballardiae* X *Helleborus* x *hybridus***
Varietal Denomination: HM 1214

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,400

(22) Filed: Nov. 14, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'HM 1214', characterized by its upright to somewhat outwardly spreading and mounded plant habit; moderately vigorous to vigorous growth habit; dark green-colored leaflets with lighter green-colored venation; freely flowering habit; light yellow green-colored flowers; and good garden performance.

1 Drawing Sheet

Figure 1:
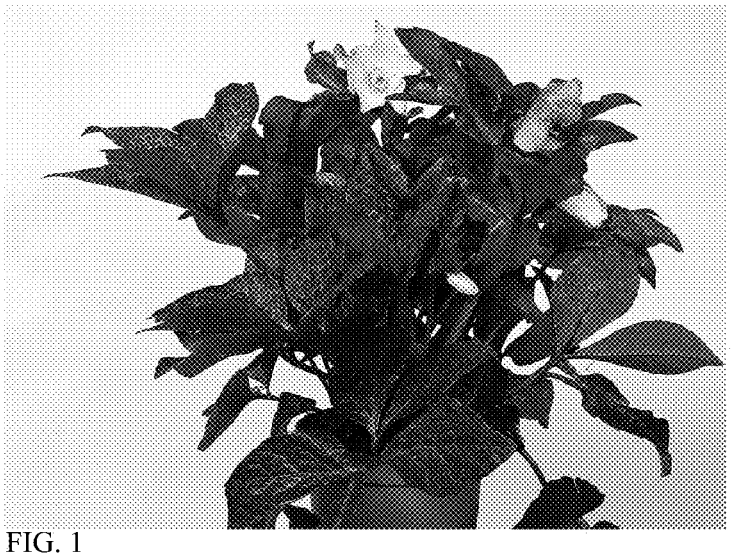

Botanical designation: *Helleborus ballardiae* X *Helleborus* x *hybridus.*

Cultivar denomination: 'HM 1214'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1377. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ballardiae* X *Helleborus* x *hybridus* and hereinafter referred to by the name 'HM 1214'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in December, 2014 of a proprietary selection of *Helleborus ballardiae* identified as code number P482, not patented, as the female, or seed, parent and a proprietary selection of *Helleborus* x *hybridus* identified as code number O1577, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2017.

Asexual reproduction of the new *Helleborus* plant by in vitro axillary meristem culture in a controlled environment in Glandorf, Germany since April, 2017 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HM 1214'. These characteristics in combination distinguish 'HM 1214' as a new and distinct *Helleborus* plant:

1. Upright to somewhat outwardly spreading and mounded plant habit.
2. Moderately vigorous to vigorous growth habit.
3. Dark green-colored leaflets with lighter green-colored venation.
4. Freely flowering habit.
5. Light yellow green-colored flowers.
6. Good garden performance.

Plants of the new *Helleborus* differ from plants of the female parent selection in the following characteristics:

1. Leaf venation of leaflets of plants of the new *Helleborus* is more distinct than leaf venation of leaflets of plants of the female parent selection.

2. Flowers of plants of the new *Helleborus* are light yellow green in color whereas flowers of plants of the female parent selection are creamy white to pink in color.

Plants of the new *Helleborus* differ from plants of the male parent selection in the following characteristics:

1. Leaf venation of leaflets of plants of the new *Helleborus* is more distinct than leaf venation of leaflets of plants of the male parent selection.
2. Flowers of plants of the new *Helleborus* are light yellow green in color whereas flowers of plants of the male parent selection are white in color.

Plants of the new *Helleborus* can also be compared to plants of *Helleborus* x *ericsmithii* X *Helleborus* x *hybridus* 'COSEH 4200', disclosed in U.S. Plant Pat. No. 28,297. In side-by-side comparisons, plants of the new *Helleborus* differ primarily from plants of 'COSEH 4200' in the following characteristics:

1. Leaf venation of leaflets of plants of the new *Helleborus* is more distinct than leaf venation of leaflets of plants of 'COSEH 4200'.
2. Flowers of plants of the new *Helleborus* are light yellow green in color whereas flowers of plants of 'COSEH 4200' are pink in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HM 1214' grown in a container.

Figure 2:
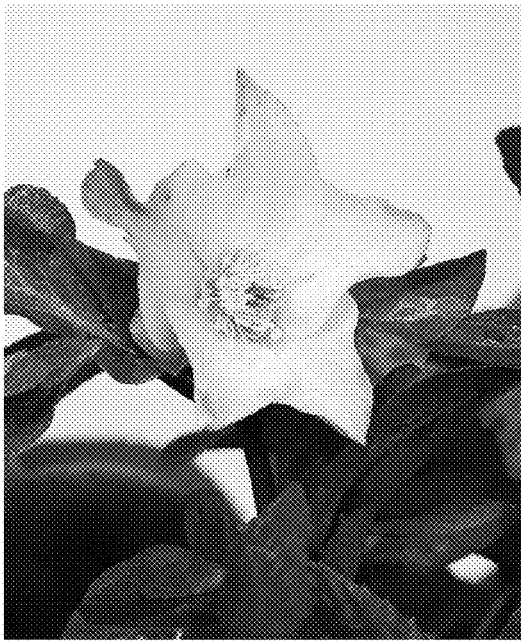

The photograph at the bottom of the sheet (FIG. 2) is a close-up view of a typical flowering plant of 'HM 1214'.

DETAILED BOTANICAL DESCRIPTION

The aforementioned photographs and following observations, measurements and values describe plants grown during the late autumn in 17-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ballardiae* X *Helleborus* x *hybridus* 'HM 1214'.

Parentage:

*Female, or seed, parent*.—Proprietary selection of *Helleborus ballardiae* identified as code number P482, not patented.

*Male, or pollen, parent*.—Proprietary selection of *Helleborus* x *hybridus* identified as code number O1577, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within to slightly above the foliar plane; plant shape, roughly globular; moderately vigorous to vigorous growth habit and moderate growth rate.

*Plant height, soil level to top of foliar plane*.—About 29.5 cm.

*Plant height, soil level to top of flowers*.—About 33.9 cm.

*Plant diameter* (*area of spread*).—About 52 cm.

Leaf description:

*Arrangement*.—Leaves arranged in a basal rosette; leaves palmately compound with typically five, or occasionally three, leaflets per leaf.

*Leaf length*.—About 17.2 cm.

*Leaf width*.—About 20.9 cm.

*Leaflet length*.—About 11.9 cm.

*Leaflet width*.—About 7.2 cm.

*Leaf shape*.—Palmate; roughly reniform in outline.

*Leaflet shape*.—Elliptic to ovate, occasionally obovate.

*Leaflet apex*.—Acute.

*Leaflet base*.—Attenuate.

*Leaflet margin*.—Serrate; slightly to moderately coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; moderately glossy to glossy.

*Leaflet venation pattern*.—Pinnate and reticulate.

*Leaflet color*.—Developing leaflets, upper surface: Close to 137A; towards the base, tinged with close to 183A; venation, close to N144D. Developing leaflets, lower surface: Close to 148A strongly tinged with close to N200A; venation, close to 187A. Fully developed leaflets, upper surface: Slightly darker than a blend of 139A and 147A; towards the base, tinged with close to a blend of N186C and 200A; venation, close to 144A. Fully developed leaflets, lower surface: Close to 147B; venation, close to 187A.

*Petioles*.—Length: About 18.4 cm. Diameter: About 5 mm by 5.5 mm. Strength: Strong. Texture and luster, upper and lower surfaces: Smooth, glabrous; moderately glossy. Color, upper surface: Close to 146B; moderately to heavily covered with fine dots, close to 200A. Color, lower surface: Close to 146B; moderately to heavily covered with fine dots, close to 200C.

Flower description:

*Flower shape and habit*.—Single rotate bowl-shaped flowers arranged in panicles; freely flowering habit with about seven flowers per inflorescence and about 21 flowers and flower buds per plant; flowers face mostly outwardly to slightly nodding.

*Fragrance*.—None detected.

*Natural flowering season*.—Plants begin flowering about ten months after planting; plants flower naturally from late autumn into the winter in Germany.

*Flower longevity on the plant*.—About ten days; sepals persistent, other flower parts are not persistent.

*Flower buds*.—Length: About 2.7 cm. Diameter: About 1.2 cm. Shape: Narrowly elliptic to oblong. Texture and luster: Smooth, glabrous; matte. Color: Close to a blend of 145D and 150D; towards the base, tinged with close to 182B.

*Inflorescence height* (*including peduncle*).—About 34.1 cm.

*Inflorescence diameter*.—About 15.9 cm.

*Flower diameter*.—About 8.2 cm.

*Flower depth*.—About 3.7 cm.

*Petals*.—All petals are transformed into nectaries.

*Sepals*.—Quantity and arrangement: About five, arranged in a single whorl. Length: About 4.6 cm. Width: About 3.7 cm. Shape: Broadly ovate to close to elliptic; slightly concave. Apex: Broadly acute to narrowly obtuse. Base: Cuneate. Margin: Entire. Texture and luster, upper surface: Smooth, glabrous; matte. Texture and luster, lower surface: Smooth, glabrous; slightly glossy. Color: When opening, upper surface: Close to 157B to 157C; towards the margins, close to 155C. When opening, lower surface: Close to 150D; towards the apex, close to 154D; towards the base, tinged with close to 182C. Fully opened, upper surface: Close to a blend of 150D and 157C; towards the apex, close to 154C and tinged with close to 184C; venation, similar to lamina colors; with subsequent development, color becoming closer to N144A, towards the margins and apex, strongly tinged with close to 179B. Fully opened, lower surface: Close to a blend of 150D and 157B; towards the apex, close to 154C to 154D; towards the apex and base, tinged with close to 184C to 184D; venation, similar to lamina colors; with subsequent development, color becoming closer to N144B strongly tinged with close to 178C.

*Flower bracts*.—Quantity per flower: Typically one. Length: About 8 cm. Width: About 4.5 cm. Shape: Ovate to broadly obovate. Apex: Acute to three-parted. Base: Truncate to cuneate. Margin: Proximally, entire; distally, serrate; coarsely undulate. Color, upper surface: Close to NN137A; venation, close to 144A; midvein, tinged with close to 187A. Color, lower surface: Close to 148A, strongly tinged with close to 200B to 200C; midvein, close to 183A.

*Peduncles*.—Length: About 27.3 cm. Diameter: About 8 mm to 9 mm. Aspect: About 12.5 degrees from vertical. Strength: Strong. Texture and luster: Smooth, glabrous; moderately glossy. Color: Close to 146B; heavily covered with fine dots, close to 183B and 183C.

*Pedicels*.—Length: About 2 cm. Diameter: About 2.5 mm. Aspect: About 35 degrees from peduncle axis. Strength: Moderately strong. Texture and luster: Sparsely to moderately pubescent; slightly glossy. Color: Close to 150C and 150D; heavily covered with fine dots, close to 183A and 183B.

*Reproductive organs*.—Stamens: Quantity per flower: About 75. Filament length: About 1.7 cm. Filament color: Close to 150D. Anther shape: Double and broadly reniform; basifixed. Anther size: About 2 mm by 3.5 mm. Anther color: Close to 150C. Pollen amount: Sparse. Pollen color: Close to 4D to lighter than 4D. Pistils: Quantity per flower: About four to six. Pistil length: About 1.3 cm. Stigma diameter: About 0.3 mm. Stigma shape: Club-shaped. Stigma color: Close to 150D. Style length: About 1.25 cm. Style color: Close to 185C. Ovary color: Close to 145C. Nectaries (transformed petals): Quantity per flower: About 11 to 13. Length: About 9 mm. Diameter: About 3 mm. Shape: Tubular, flattened; apices, obtuse. Texture and luster, inner and outer surfaces: Smooth, glabrous; slightly glossy. Color, immature, inner and outer surfaces: Close to N144D; towards the apex, close to 150B and towards the base, close to 146C. Color, mature, inner and outer surfaces: Close to 146D; towards the apex, close to 150B and towards the base, close to 146C; with subsequent development, color becoming closer to N144A, towards the apex, close to 153C and towards the base, close to 146C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HM 1214' as illustrated and described.

* * * * *